United States Patent
Mustafa et al.

(10) Patent No.: US 11,364,122 B2
(45) Date of Patent: Jun. 21, 2022

(54) TISSUE ENGINEERING SCAFFOLDS

(71) Applicant: VESTLANDETS INNOVASJONSSELSKAP AS, Bergen (NO)

(72) Inventors: Kamal Babikeir Eln Mustafa, Bergen (NO); Ahmad Rashad Saad Mohamed Elsebahy, Bergen (NO); Anna Finne Wistrand, Stockholm (SE); Yang Sun, Shanghai (CN); Alexander Franciscus Van Tol, Potsdam (DE)

(73) Assignee: VESTLANDETS INNOVASJONSSELSKAP AS, Bergen (NO)

( * ) Notice: Subject to any disclaimer, the term of this patent is extended or adjusted under 35 U.S.C. 154(b) by 71 days.

(21) Appl. No.: 16/492,504

(22) PCT Filed: Mar. 12, 2018

(86) PCT No.: PCT/EP2018/056124
§ 371 (c)(1),
(2) Date: Sep. 9, 2019

(87) PCT Pub. No.: WO2018/162764
PCT Pub. Date: Sep. 13, 2018

(65) Prior Publication Data
US 2020/0261230 A1    Aug. 20, 2020

(30) Foreign Application Priority Data
Mar. 10, 2017    (GB) ..................... 1703832

(51) Int. Cl.
*A61F 2/30*    (2006.01)
*A61F 2/28*    (2006.01)

(52) U.S. Cl.
CPC ........ *A61F 2/30756* (2013.01); *A61F 2/3094* (2013.01); *A61F 2/2846* (2013.01);
(Continued)

(58) Field of Classification Search
CPC .. A61F 2002/30235; A61F 2002/30766; A61F 2/2846; A61F 2/30734; A61F 2002/30738
See application file for complete search history.

(56) References Cited

U.S. PATENT DOCUMENTS

| | | | |
|---|---|---|---|
| 5,211,664 | A | 5/1993 | Tepic et al. |
| 6,530,956 | B1 | 3/2003 | Mansmann |

(Continued)

FOREIGN PATENT DOCUMENTS

| | | |
|---|---|---|
| CN | 201624812 U | 11/2010 |
| EP | 1800627 A2 | 6/2007 |

(Continued)

OTHER PUBLICATIONS

Examination Report for United Kingdom Patent Application No. GB1703832.4, dated Aug. 27, 2019, 5 pages.
(Continued)

*Primary Examiner* — Javier G Blanco
(74) *Attorney, Agent, or Firm* — Withrow & Terranova, P.L.L.C.; Vincent K. Gustafson (57) ABSTRACT

A scaffold (12) for tissue engineering comprises an inner portion (14), an outer portion (16), and a base portion (22) connecting the inner portion and the outer portion. The inner portion (14) comprises a channel (18) surrounded by a first set of one or more walls. The outer portion (16) comprises a second set of one or more walls. The portions are arranged such that the second set of one or more walls substantially surrounds the first set of one or more walls with a spacing between the first and second sets of walls defining a cavity (20) between the inner portion (14) and the outer portion
(Continued)

(16). The inner portion (14) and the outer portion (16) may have different shapes; and/or the scaffold (12) may further comprise a filler material in the cavity (20) defined between the inner and outer portions.

12 Claims, 4 Drawing Sheets (52) U.S. Cl.
CPC ... *A61F 2/30734* (2013.01); *A61F 2002/3097* (2013.01); *A61F 2002/30766* (2013.01); *A61F 2002/30962* (2013.01); *A61F 2002/30968* (2013.01); *A61F 2002/30985* (2013.01); *A61F 2310/00005* (2013.01)

(56) References Cited

U.S. PATENT DOCUMENTS

| | | | |
|---|---|---|---|
| 6,730,252 | B1 | 5/2004 | Teoh et al. |
| 7,837,735 | B2 * | 11/2010 | Malone .................. A61F 2/446 623/17.16 |
| 2004/0225360 | A1 | 11/2004 | Malone |
| 2005/0015154 | A1 | 1/2005 | Lindsey et al. |
| 2007/0203584 | A1 | 8/2007 | Bandyopadhyay et al. |
| 2008/0206297 | A1 | 8/2008 | Roeder et al. |
| 2011/0307073 | A1 * | 12/2011 | Teoh ....................... A61L 27/54 623/23.61 |
| 2015/0196371 | A1 | 7/2015 | Westover |
| 2016/0067375 | A1 | 3/2016 | Holmes et al. |
| 2016/0287391 | A1 | 10/2016 | Larsen et al. |

FOREIGN PATENT DOCUMENTS

| | | |
|---|---|---|
| EP | 2039327 A1 | 3/2009 |
| WO | 99039724 A1 | 8/1999 |
| WO | 02049548 A1 | 6/2002 |
| WO | 02083194 A1 | 10/2002 |
| WO | 2008082766 A2 | 7/2008 |
| WO | 2010044758 A1 | 4/2010 |
| WO | 2015106247 A1 | 7/2015 |
| WO | 2017031167 A1 | 2/2017 |

OTHER PUBLICATIONS

Notification of Transmittal of the International Search Report and Written Opinion (Form PCT/ISA/220), International Search Report (Form PCT/ISA/210), and Written Opinion of the International Searching Authority (Form PCT/ISA/237) for International Application No. PCT/EP2018/056124, dated Jun. 13, 2018, 18 pages.
Search Report under Section 17(5) for United Kingdom Patent Application No. GB1703832.4 dated Jul. 20, 2017, 4 pages.
Kim et al., "Composite System of PLCL Scaffold and Heparin-Based Hydrogel for Regeneration of Partial-Thickness Cartilage Defects," Biomacromolecules, vol. 13, pp. 2287-2298, American Chemical Society, Jul. 3, 2012.
Thayer et al., "Cellularized Cylindrical Fiber/Hydrogel Composites for Ligament Tissue Engineering," Biomacromolecules, vol. 15, pp. 75-83, American Chemical Society, Nov. 24, 2013.
Yassin et al., "Cell seeding density is a critical determinant for copolymer scaffolds-induced bone regeneration," Journal of Biomedical Materials Research Part A, vol. 103A, Issue 11, pp. 3649-3658, Wiley Periodicals, May 2015.
First Office Action for Chinese Patent Application No. 201880026876.X dated Apr. 8, 2021, 20 pages including English translation.
Second Office Action for Chinese Patent Application No. 201880026876.X dated Nov. 30, 2021, 16 pages including English translation.
Examination Report for European Patent Application No. 18711088.7, dated Nov. 16, 2020, 5 pages.
Examination Report for European Patent Application No. 18711088.7, dated Nov. 11, 2021, 4 pages.
Search Report for Japanese Patent Application No. 2019571105, dated Sep. 22, 2021, 27 pages.
Notice of Reasons for Refusal for Japanese Patent Application No. 2019571105, dated Oct. 5, 2021, 8 pages.

* cited by examiner

TISSUE ENGINEERING SCAFFOLDS

This application is a 35 U.S.C. § 371 national phase filing of International Application No. PCT/EP2018/056124 filed on Mar. 12, 2018, and further claims priority to United Kingdom Patent Application No, 1703832.4 filed on Mar. 10, 2017, wherein the disclosures of the foregoing applications are hereby incorporated by reference herein in their respective entireties.

The present invention relates to devices and methods for tissue engineering using a scaffold.

Tissue engineering generally relates to the growth of new connective tissues, or organs, from living cells using a scaffold as a support during growth. Tissue engineering techniques may be used to produce an organ or tissue graft for implantation back into a donor host. Tissue engineering frequently involves stem cells; implanting stem cells in an appropriate location can generate bone, tendon and cartilage. Applications include dermal wound healing and repair of cartilage, ligament or bone.

Bone regeneration or repair typically involves the implantation of a bone graft. However the failure rate of bone grafts can be high. In bone tissue engineering, the osteogenic and angiogenic potential of stem cells in 3D structural systems has been demonstrated in vitro and in vivo. A classic tissue engineering treatment uses bone cells carried by a synthesized scaffold to accelerate healing procedures. The environment for bone regeneration is very complicated, including different cell types, growth factors, nutrition supply and mechanical stimulation.

It has been found that the porosity of a three-dimensional bone graft scaffold can play a critical role in bone regeneration in in vivo situations. The greater the porosity the more successful is bone cell growth, but this can adversely affect the mechanical stability of the scaffold. It is particularly important for the scaffold to be biomechanically stable for load-bearing tissues such as bone and cartilage.

It is known to form bone grafts from biocompatible and biodegradable scaffolds that can support cell living functionality during osteogenesis. Scaffolds made from ceramic, synthetic polymer, metal or hydrogel have been previously proposed. For example, ceramic scaffolds such as macroporous hydroxyapaptite (HA) have been tried with some clinical success. However, ceramics are relatively brittle materials and such scaffolds are prone to fracture; furthermore ceramic materials may not be readily resorbable.

Research has shown that the first generations of copolymer scaffolds were biocompatible both in vitro and in vivo, with the main disadvantages being the lack of biological cues promoting angiogenesis and osteogenesis. Furthermore, the manual intervention required, the lack of scaffold reproducibility, and the mechanical properties to some extent are drawbacks of typical scaffold fabrication techniques such as solvent-casting/particulate-leaching and electrospinning.

U.S. Pat. No. 8,702,808 describes a scaffold implant comprising a porous tubular scaffold. The scaffold is made from porous bioresorbable polymer or polymer composite, such as polycaprolactone (PCL) or PCL-ceramic composite mesh. The scaffold is made from layers of micro-filament meshes so as to form interconnected pores.

There remains a need for tissue engineering scaffolds that combine desirable properties in terms of porosity, mechanical stability and shape.

According to a first aspect of the present invention there is provided a device for tissue engineering comprising a scaffold, the scaffold comprising:

an inner portion comprising a channel surrounded by a first set of one or more walls;

an outer portion comprising a second set of one or more walls and arranged such that the second set of one or more walls substantially surrounds the first set of one or more walls with a spacing between the first and second sets of one or more walls defining a cavity between the inner portion and the outer portion; and a base portion connecting the inner portion and the outer portion.

Thus there is provided a device comprising a three-dimensional (3D) scaffold having a construction that has been found particularly suitable for rapid prototyping (RP) or other computer-controlled fabrication techniques. The 3D shape of the scaffold may be easily reproduced from computer aided design (CAD) data or models. The shape and/or dimensions of the scaffold can be reproduced consistently and within relatively narrow ranges of tolerance. Quality control can thereby be assured for mass production.

Furthermore, the 3D shape of the scaffold may be readily customised for different tissue engineering applications. For example, the 3D scaffold may be designed and shaped to fit in a bioreactor for modelling of tissue engineering processes. For example, the 3D scaffold may be designed and shaped to mimic a natural bone environment for drug testing ex vivo. The channel defined by the inner portion may, for example, allow for the exchange of ions, flow of oxygen, or transport of proteins, glucoses, or drugs diffused from a culture medium that is supported by the scaffold.

For example, an implantable 3D scaffold may be designed and shaped to match an existing bone in a living target, with non-invasive imaging methods like CT and MRI being used to build a CAD model for fabrication. The 3D scaffold can be used e.g. implanted as a support for in vivo growth of stem cells and/or vessels. As compared to previous attempts to make a 3D scaffold, it is an advantage of this device that the inner and outer portions are separate components of the scaffold which are connected together by the base portion. This means that various factors such as the shape, material, porosity, mechanical strength, etc. of the independent inner and outer portions can be adjusted so that the inner portion and outer portion are respectively optimised for different functions.

Figures 1A, 1B, 1C:
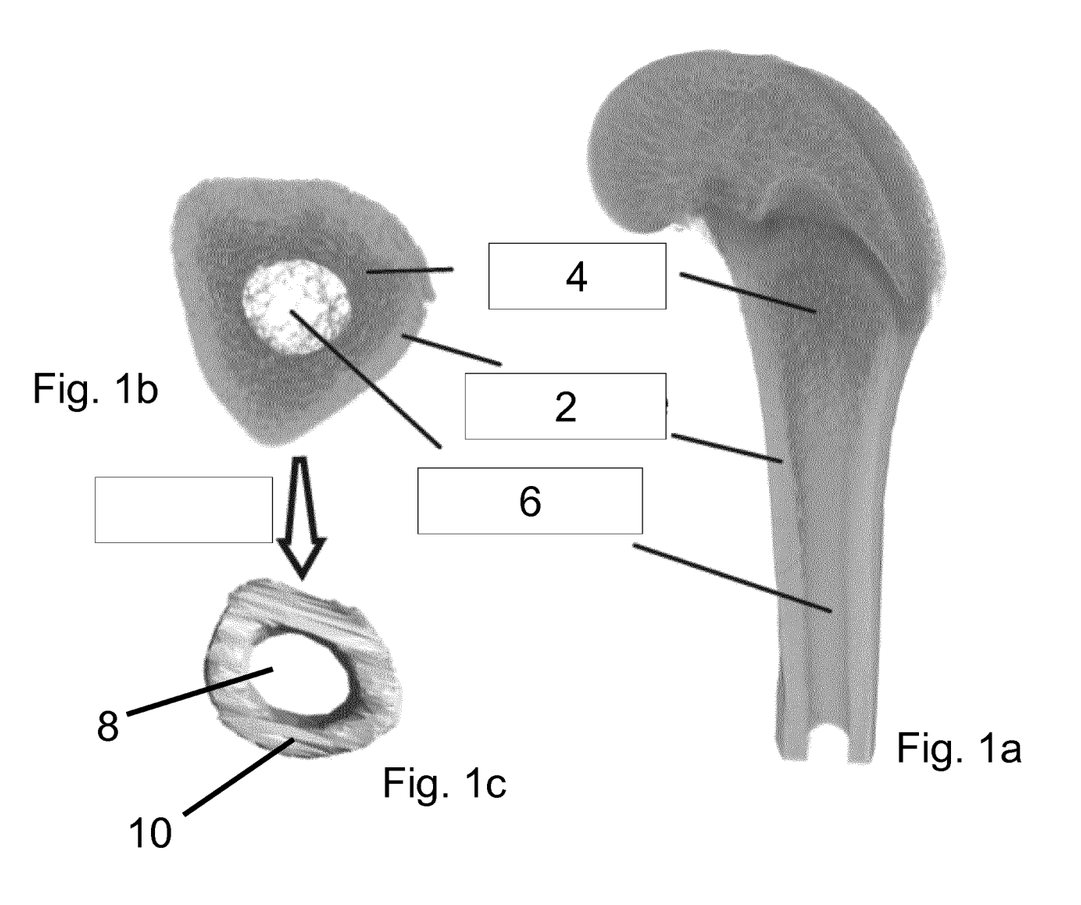
FIGS. 1a-1c schematically show how a scaffold shape can be modelled on a long bone such as a femur.

Such a device may be used for tissue engineering to form bone or other bodily tissue e.g. cartilage. The applicant has recognised the benefits of a scaffold having a shape which mimics the natural anatomical structure of bone. Typical bone anatomy is described below in relation to FIG. 1. The channel defined by the wall(s) of the inner portion may be sized and/or shaped to substantially match the medullary cavity, that is, the central area inside any bone (long, flat, etc.) that holds the bone marrow. The cavity defined between the inner portion and the outer portion may be sized and/or shaped to substantially match the spongy bone that surrounds the medullary cavity. The wall(s) of the outer portion may be sized and/or shaped to substantially match the compact bone forming the outside of any bone. The mechanical stability of the scaffold is assured by the base portion that connects the inner and outer portions. When such a scaffold is implanted for regeneration of an existing bone, the outer portion can transmit mechanical forces to/from the compact bone while the channel inside the inner portion can provide a conduit for nutrients to be carried to/from the bone marrow in the medullary cavity. Accordingly a device as described herein can be optimised for bone regeneration.

The 3D shape of the scaffold is mainly determined by the design of the inner and outer portions. As is mentioned above, it is a significant advantage of the device that the inner and outer portions can be designed and fabricated independently of one another. Both the inner portion and the outer portion may have any suitable three-dimensional shape. While the second set of one or more walls substantially surrounds the first set of one or more walls, the outer portion is not necessarily continuous. For example, the outer portion may comprise two horseshoe portions with a small gap between them or multiple wall portions at spaced intervals. However, in a preferred set of embodiments, the outer portion comprises a continuous second set of one or more walls. This means that a filler material (as will be described further below) can be contained by the second set of walls in the cavity defined between the inner and outer portions. In addition, or alternatively, the inner portion preferably comprises a continuous first set of one or more walls. This may also assist in containing a filler material in the cavity defined between the inner and outer portions. In preferred embodiments the outer portion and/or the inner portion comprises a continuous annular wall. Of course the annular wall may have any suitable ring-like shape when viewed from above or in cross-section, e.g. circular, oval, elliptical, triangular, square, rectangular, polygonal, etc. and, furthermore, the inner portion and the outer portion may have substantially the same shape or the inner portion and the outer portion may have different shapes. In one example, the inner portion may comprise a triangular channel surrounded by the first set of walls and the outer portion may comprise a cylindrical wall surrounding the triangular channel, i.e. with the cavity defined by the spacing there between.

The second set of walls of the outer portion may not be arranged symmetrically around the first set of walls of the inner portion. For instance, this may result in a non-constant or varying spacing around the circumference of the cavity. In practice such a device may be harder to fabricate but the scaffold may be more likely to match the cross-sectional shape of natural bone. However, in at least some embodiments, the outer portion is arranged substantially symmetrically around the inner portion. This can assist in ease of fabrication and/or construction of the scaffold. In one set of examples the scaffold comprises a rotationally symmetrical arrangement of the outer portion and inner portion. In one set of examples the second set of one or more walls is arranged concentrically around the first set of walls. The outer portion and inner portion may therefore be arranged concentrically around the same central axis, for example a central axis defined by the channel.

The one or more walls of the outer portion and/or the inner portion may be contoured or stepped. In one set of embodiments the one or more walls of the outer portion and/or the inner portion may be tapered, for example to match the tapered shape of natural bone, e.g. a long bone such as the femur. In another set of embodiments the one or more walls of the outer portion and/or the inner portion may be substantially straight.

The one or more walls of the outer portion and/or the inner portion can have any suitable length. The first set of wall(s) of the inner portion may have the same length as, or a different length to, the second set of wall(s) of the outer portion. Either of the first and second sets of wall(s) may extend further than the other. The length of the walls forming the inner and outer portions of the scaffold may be chosen independently of any diameter of the inner portion and/or outer portion. However, in at least some embodiments, the one or more walls of the outer portion and/or the inner portion have a length that is less than the diameter of the outer portion and/or the inner portion. For example, the first set of one or more walls of the inner portion has a first length that is less than a diameter of the inner portion. For example, the second set of one or more walls of the outer portion has a second length that is less than a diameter of the outer portion. The first length may be the same as the second length. This means that the scaffold has a generally flat, rather than elongate, shape. By minimising the length of the walls compared to the diameter the outer portion and/or the inner portion, the channel and the cavity are kept relatively wide so as not to unduly constrict the flow of matter (e.g. cells, nutrients, drugs, proteins, etc.) through the scaffold when the device is in use.

In a first set of embodiments, for example where the 3D scaffold is be designed and shaped to fit in a bioreactor, the channel defined by the inner portion has a diameter of around 3.5 mm. Such a scaffold may also be useful in a device for animal-based tissue engineering.

In a preferred set of embodiments the channel defined by the inner portion has a diameter that is substantially matched to a diameter of the medullary cavity in a bone into which the device is to be implanted. The diameter can be varied and customized according to anatomical variations between individuals, such as gender, weight, age. The average human bone medullary cavity is 20 mm. In at least some examples, the diameter of the channel may be around 15, 16, 17, 18, 19, 20, 21, 22, 23, 24 or 25 mm.

In a first set of embodiments, for example where the 3D scaffold is be designed and shaped to fit in a bioreactor, the cavity defined between the inner and outer portions may have an inner diameter of about 3.5 mm and an outer diameter of about 11.4 mm. In at least some examples, the diameter of the outer portion may be 11.4 mm.

In a preferred set of embodiments the cavity defined between the inner and outer portions has an inner and/or outer diameter that is substantially matched to a diameter of the spongy bone in a bone into which the device is to be implanted. For example, the cavity may have an inner diameter of about 20 mm and an outer diameter of about 25, 26, 27, 28, 29 or 30 mm. This can again be varied according to individual anatomy, i.e custom-made scaffolds.

In a preferred set of embodiments the outer portion has a diameter that is substantially matched to a diameter of the compact bone in a bone into which the device is to be implanted. In at least some examples, the diameter of the outer portion may be about 26, 27, 28, 29 or 30 mm For example, these diameters may be chosen based on one or more measurements taken from an image of the bone into/onto which the device is to be implanted/grafted, e.g. varied according to the measurements performed by CT scan. The average diameter of a human femur is 28.4 mm.

The Applicant has recognised that it can be important for the scaffold to provide sufficient porosity to functionally support cell proliferation and enable the flow of materials into/out of the cavity and/or the channel. One possibility could be to form the inner portion and/or outer portion from a porous material. Another possibility could be to form the inner portion and/or outer portion from a porous structure. One example of a porous structure comprises layers of mesh, for example micro-filament meshes. However the Applicant has further recognised that a problem with many porous materials and/or porous structures is that the pore size is not uniform and the porosity can vary across a relatively wide range, making it difficult if not impossible to ensure reproducibility between scaffolds and devices. For example, scaffolds made from layers of micro-filament meshes have a randomly interconnected porous structure which is non-uniform and unreproducible. It is therefore preferable that the first set of one or more walls defining the inner portion consists of a substantially solid material comprising a plurality of apertures in the first set of one or more walls. In addition, or alternatively, it is preferable that the outer portion consists of a substantially solid material comprising a plurality of apertures in the second set of one or more walls. Advantageously, this means that the inner and/or outer portions can provide the scaffold with porosity without detracting from mechanical strength. Further preferably the plurality of apertures is formed during fabrication of the scaffold. Accordingly the number, distribution, size and/or spacing of the apertures can be controlled during the fabrication process. This can result in much tighter control over the porosity of the scaffold and reproducibility of the device.

In a preferred set of embodiments the first set of one or more walls of the inner portion comprises a plurality of apertures arranged in a first set of layers spaced along the length of the wall(s) by a first interval. Preferably the layers are evenly spaced by the first interval along the length of the wall(s). In a preferred set of embodiments the second set of one or more walls of the outer portion comprises a plurality of apertures arranged in a second set of layers spaced along the length of the wall(s) by a second interval. Preferably the layers are evenly spaced by the second interval along the length of the wall(s). The second spacing interval in the second set of layers may be the same as the first spacing interval in the first set of layers. Further preferably the first set of layers may be arranged to coincide with the intervals between the second set of layers, and the second set of layers may be arranged to coincide with the intervals between the first set of layers. In other words, the apertures in the inner portion may be formed in alternate layers to the apertures in the outer portion. By alternating the axial position of the apertures between the inner and outer portions along the length of the scaffold, there is never a straight path between the openings in the walls and hence no planes of weakness in the device.

The intervals between the first and/or second sets of aperture layers may have a height or thickness of 100-800 µm. By providing substantial intervals between the apertures in the otherwise solid material of the inner portion and/or the outer portion, the mechanical strength of the scaffold is not unduly weakened.

In the inner portion and/or the outer portion, each layer of apertures may be spaced along the length of the wall(s) by an interval that is not less than the height of the apertures. In other words, the height of each aperture may be equal to, or less than, the interval between adjacent layers of apertures. For example, each aperture may have a height in the range of 100-800 µm. In addition, or alternatively, each layer preferably comprises a plurality of apertures spaced (equally or unequally) around the circumference of the inner portion. The width of each aperture may be less than a distance between adjacent apertures in the same layer. Either or both of these features can help to ensure that the inner portion and/or the outer portion is not unduly weakened by the presence of the apertures in the wall(s) of the scaffold.

The first set of one or more walls of the inner portion may have substantially the same thickness as the second set of one or more walls of the outer portion. Note that in a concentric arrangement of the inner and outer portions, according to a set of examples mentioned above, the thickness of the first and/or second set of one or more walls may be defined as the width of the walls as measured in a radial direction from the central axis of the concentric arrangement. However the Applicant has recognised that it may be beneficial for the second set of one or more walls to be thicker than the first set of one or more walls. This can ensure that the outer portion has greater mechanical strength or rigidity than the inner portion. This can be important when the device is to be implanted or used in vivo, for example to grow a bone graft, as the outer portion is then aligned with the compact bone and preferably transmits load forces to/from the existing bone. To assist ease of fabrication of the device by rapid prototyping techniques such as 3D printing, wherein the walls may be built up by successively deposited layers of material, the second set of walls may be x times thicker than the first set of one or more walls, wherein x is an integer, e.g. 2, 3, 4, etc. In a set of examples the second set of walls is twice as thick as the first set of one or more walls.

As will be described in more detail below, the first set of one or more walls of the inner portion may be formed from a first material that is the same as, or different to, a second material forming the second set of one or more walls of the outer portion.

The base portion may have any suitable shape or form as long as it acts to physically connect the inner portion and the outer portion. The base portion may, for example, help to set the spacing between the first and second sets of one or more walls which defines the cavity between the inner portion and the outer portion. The base portion may be substantially solid or it may include one or more apertures. For example, the base portion could comprise an arrangement of discrete spacers connected between the inner and outer portions. In a concentric arrangement of the inner and outer portions, according to a set of examples mentioned above, the base portion may comprise a plurality of spokes extending radially outwardly from the inner portion to the outer portion. However it is preferable that the base portion can act as a support for any filler material contained in the cavity and hence the base portion may extend substantially continuously between the inner portion and the outer portion.

In addition, or alternatively, the base portion preferably extends in a plane substantially perpendicular to the inner portion and/or outer portion. In one set of examples, the base portion comprises a spacer plate extending between the inner portion and the outer portion. The spacer plate may have any suitable shape, for example circular, oval, square, rectangular, polygonal or irregular. The shape of the spacer plate may or may not match the shape of the inner portion and/or outer portion. However in one example the spacer plate comprises a circular plate arranged substantially symmetrically about a central axis defined by the channel. The base portion, whether in the form of a spacer plate or otherwise, may be substantially flat. The inner portion and the outer portion may therefore be aligned so as to be connected in the plane of the base portion. The base portion, whether in the form of a spacer plate or otherwise, may have a diameter that is greater than a diameter of the outer portion. The base portion may therefore provide a support not only for any filler material contained in the cavity but also for any tissue material growing around the outside of the scaffold. In addition, or alternatively, the base portion extending beyond the outer portion may help to strength the scaffold and/or provide for ease of handling. In addition, or alternatively, the base portion extending beyond the outer portion may help to fit the device to different types of bioreactors. For example, the base portion may have an outer diameter of up to 15 mm so as to fit bioreactor systems containing 24-well or 48-well microtiter plates.

As is discussed above, the scaffold is preferably designed to mimic natural bone structure and the channel defined by the inner portion may imitate the medullary cavity of bone. The base portion preferably comprises a window at least partially aligned with the channel. The window may comprise a material that is more porous than the rest of the base portion or, preferably, the window may comprise an opening in the base portion. The window can therefore provide a flow path through the base portion e.g. so that blood cells and nutrients can flow along the channel and then diffuse outwardly from the inner portion through the rest of the scaffold. In at least some examples the window is aligned with the channel and preferably has the same size and/or shape. For example, if the inner portion comprises a triangular channel then the base portion may comprise a triangular window to match.

The base portion may be formed from any suitable material, for example a material that is solid, porous or semi-porous. As is mentioned above, the base portion preferably acts to support any filler material contained in the cavity. In one set of embodiments the base portion consists of a substantially solid material. For example, the base portion may comprise or consist of one or more materials such as calcium phosphate (e.g. tricalcium phosphate, hydroxyapatite, etc.) or bioglass. Accordingly the base portion, optionally together with the inner portion and/or outer portion, may advantageously contribute to the mechanical strength and rigidity of the scaffold. A substantially solid base portion may be particularly suitable if the device is intended to be used in vitro, for example for drug testing purposes.

In another set of embodiments the base portion consists of a substantially porous material. For example, the base portion may comprise or consist of a mesh, e.g. a micro-filament mesh. This may be particularly suitable if the device is intended to be implanted in vivo, for example to support a bone graft. The porosity of the base portion may be chosen based on a number of factors, such as the type of tissue cells to be supported by the scaffold, and diffusion of desired materials to/from the supported cells.

The base portion may be formed from a material that is the same as, or different to, the one or more materials forming the inner portion and/or outer portion. Some suitable polymeric materials are described further below.

Various materials may be suitable for making the scaffold, including ceramics, polymers, metals and hydrogels. However, as is outlined above, it is an aim of the present invention to provide a device that is strong, robust and capable of being formed by rapid prototyping techniques such as 3D printing. It is therefore preferable that the scaffold is formed from a polymeric material (including polymer-based composites). In many embodiments it is preferable for the scaffold to comprise or consist of one or more bioresorbable and/or biocompatible polymers. Such polymers may be natural or synthetic. The scaffold is therefore well-suited for in vivo applications such as creating bone grafts, although in vitro applications may also benefit from the device being bioresorbable and/or biocompatible, for example when modelling the natural bone environment in a bioreactor. The inner portion and/or the outer portion of the scaffold may be formed from one or more polymeric materials including, but not limited to: polylactides, polyglycolides, polycaprolactones, polyanhydrides, polyamides, polyurethanes, polyesteramides, polyorthoesters, polydioxanones, polyacetals, polyketals, polycarbonates, polyorthocarbonates, polyphosphazenes, polyhydroxybutyrates, polyhydroxyvalerates, polyalkylene oxalates, polyalkylene succinates, poly(malic acid), poly(amino acids), polyvinylpyrrolidone, polyethylene glycol, polyhydroxycellulose, chitin, chitosan, poly(L-lactic acid), poly(lactide-co-glycolide), poly(hydroxybutyrate-co-valerate), and copolymers, terpolymers, or combinations or mixtures of the above polymeric materials. In one set of embodiments the inner portion and/or the outer portion is formed from polylactide. In one set of embodiments the inner portion and/or the outer portion is formed from polycaprolactone (PCL).

Optionally the base portion of the scaffold may also be formed from one or more of the same polymeric materials mentioned above. Whereas the inner portion and/or outer portion preferably consist of a substantially solid material, albeit with apertures formed in the solid material according to various preferred embodiments, the base portion may comprise or consist of a substantially porous material. In at least some embodiments the base portion is made as a micro-filament mesh. Many of the polymers mentioned above, such as PCL, are suitable for forming a micro-filament mesh.

Preferably the one or more polymeric materials forming the scaffold are biocompatible, osteoconductive and/or bone-bonding (bioactive). This means that the scaffold can be used to culture undifferentiated, differentiated, osteogenic or (osteo)progenitor cells that form a bone-like extracellular matrix in vitro, after which the polymeric scaffold containing the biological extracellular matrix can be placed or implanted at a site of engraftment. In any of the devices or methods described herein, the scaffold is preferably biocompatible and/or biodegradable, to assist in supporting functional cell living.

In a device according to the present invention there is a spacing between the first and second sets of one or more walls defining a cavity, for example an annular cavity, between the inner portion and the outer portion. The first and second sets of one or more walls are preferably spaced apart along their entire length, e.g. to define a continuous cavity. However it is also envisaged that the first and second sets of one or more walls may touch one another in certain places, e.g. defining a cavity with some interruptions. The cavity may have a width of at least 1 mm, 2 mm, 3 mm, 4 mm, 5 mm, 6 mm, 7 mm or 8 mm.

As is mentioned above, the scaffold may be shaped and/or sized so as to generally mimic anatomical bone structure. The channel defined by the inner portion may provide a physical channel in situ for blood vessel and nutrition diffusion to/from the bone marrow. The channel may optionally be at least partially filled with a filler material. Preferably the device comprises a filler material in the cavity defined between the inner and outer portions. The cavity may be at least partially filled with a porous filler material, for example a porous filler material that is analogous to spongy bone. In some embodiments the porosity of the filler material may be substantially matched to that of the spongy bone in a target bone structure, for example in a human bone. In some embodiments the porosity of the filler material may be greater than that of spongy bone. Preferably the porosity of the filler material is ≥95% of the porosity of spongy bone. The filler material may, for example, have an average pore size that is more than about 100 μm.

In a preferred set of embodiments the filler material preferably comprises or consists of one or more hydrogel materials. Suitable hydrogel materials includes anhydrous and hydrated natural and synthetic hydrogels. Suitable hydrogel materials may be produced by crosslinking polymer molecules (e.g. using crosslink agents) including, but not limited to: poly(acrylic acid), poly(vinyl alcohol), poly(vinylpyrrolidone), poly(ethylene glycol), polyacrylamide, hyaluronic acid, collagen, alginate, chitosan, and polysaccharides. In one set of embodiments the filler material comprises a cellulose nanofibril (CNF) hydrogel or nanocellulose hydrogel. In one set of embodiments the filler material comprises a gelatin hydrogel. For example, gelatin methacrylamide (Gel-MA) is a biodegradable and biocompatible hydrogel.

In addition, or alternatively, the filler material may comprise or consist of particles or fibrous material, e.g. to benefit multiple properties. In addition, or alternatively, the filler material may comprise or consist of a foaming structure. In at least some embodiments the filler material may be produced by electrospinning, particulate leaching, solvent casting, freeze drying, thermally-induced phase separation methods, or other techniques.

It will be appreciated that the filler material, in particular a porous filler material, is distinctly different to the material(s) forming the inner portion and/or outer portion of the scaffold. Preferably the filler material is much softer and more porous. The device may therefore rely on the first and second sets of walls that define the cavity to provide the necessary mechanical strength to contain and support the filler material.

As is mentioned above, it is an advantage of tissue engineering devices according to the present invention that the scaffold can be made in a way that is easily scaleable, so that the scaffold can be designed and made to mimic a particular bone structure in wide range of different targets. In at least some embodiments the scaffold is made using a 3D fiber deposition (3DF) method. In at least some embodiments the scaffold is made using a computer-controlled fabrication technique, such as a rapid prototyping (RP) method. Suitable RP methods include 3D printing (e.g. fused deposition modelling), selective laser sintering, and other layer-by-layer techniques. Using such techniques the scaffold design can be scaled up or down to any desired dimensions (albeit within the limit of the RP machine's resolution). In at least some embodiments the scaffold is made from/to a customised reproducible design recorded in a computer-aided design (CAD) model.

The use of such techniques to make a scaffold as described herein is considered novel and inventive in its own right. Thus according to a further aspect of the present invention there is provided a method of making a scaffold comprising an inner portion comprising a channel surrounded by a first set of one or more walls, an outer portion comprising a second set of one or more walls and arranged such that the second set of one or more walls substantially surrounds the first set of one or more walls with a spacing between the first and second sets of one or more walls defining a cavity between the inner portion and the outer portion, and a base portion connecting the inner portion and the outer portion; the method comprising: at least one of: 3D fiber deposition (3DF); 3D printing; selective laser sintering; any other layer-by-layer technique of rapid prototyping.

Such computer-controlled fabrication e.g. rapid prototyping techniques advantageously provide the scaffold with the ability to be custom-made. In a preferred set of embodiments the scaffold is customised to match the dimensions of a particular osseous environment in a human or animal target. A device comprising a customised scaffold may then be used in vivo, for example for a bone graft, or in vitro, for example as a biological model for mimicking and analysing tissue engineering processes or for analysing drug release under controlled circumstances. The custom dimensions of the scaffold may be determined using non-invasive imaging techniques such as CT or MRI.

Customisation of a scaffold as described herein is considered novel and inventive in its own right. Thus according to a further aspect of the present invention there is provided a method of making a customised scaffold for tissue engineering comprising an inner portion comprising a channel surrounded by a first set of one or more walls, an outer portion comprising a second set of one or more walls and arranged such that the second set of one or more walls substantially surrounds the first set of one or more walls with a spacing between the first and second sets of one or more walls defining a cavity between the inner portion and the outer portion, and a base portion connecting the inner portion and the outer portion; the method comprising: imaging an osseous environment in a human or animal target; and selecting one or more dimensions of the inner portion and/or outer portion to substantially match the imaged osseous environment. The imaging step preferably comprises a non-invasive imaging technique such as CT or MRI.

It will be appreciated that matching one or more dimensions of the inner portion and/or outer portion to the imaged osseous environment may comprise selecting at least one inner or outer diameter. Furthermore, the width of the channel and/or cavity may be substantially matched to the imaged osseous environment. Such customisation of the scaffold dimensions can be particularly important for implants as the environment for bone (re)generation is very complicated (including e.g. different cell types, growth factors, nutrition supply and mechanical stimulation) and the more closely the scaffold can mimic the osseous environment the more likely is the implant to be successful in bone (re)generation.

As mentioned above, the tissue engineering device and methods disclosed herein may find use in a variety of applications including, but not limited to:

Implants for tissue engineering;
Biological models for mimicking and analysing tissue engineering processes;
Biological models for analysing drug release under controlled circumstances;
Scaffold-based studies in bioreactors.

Each of these potential uses can take advantage of the unique scaffold shape and mechanical stability.

According to a further aspect of the present invention there is provided a method of tissue engineering using a device as described hereinabove. Such a method may comprise the steps of: filling the cavity defined between the inner and outer portions of the scaffold with a filler material; and seeding the scaffold with tissue cells. It will be appreciated that the cells may be introduced with the filler material or separately. As is described above, the filler material is preferably porous, for example formed from one or more hydrogel materials. The step of filling the cavity preferably comprises injecting hydrogel solution and cross-linking or freeze-drying to form the porous filler material. The porosity of the filler material allows for bone ingrowth into the scaffold, enabling the growth of bone samples (e.g. for testing in vitro) and bone implants e.g. for (re)generation in vivo. Such methods may optionally further comprise: filling the channel with a second filler material. The second filler material may be the same as or different to the filler material in the cavity. In such embodiments the channel may be filled before or after the cell seeding step.

In a first set of embodiments such methods may further comprise: growing tissue on the scaffold in vitro. For example, the device may be mounted in a bioreactor for modelling or testing purposes.

In a second set of embodiments such methods may further comprise: implanting the device (or at least the scaffold thereof) in a living target. The device according to the invention can be used for a variety of surgical treatments where osseous generation or regeneration is needed.

These include all bone defects in orthopaedics, maxillofacial surgery, dentistry and any other disciplines where osseous (re)generation is required. The device can also be used for guided tissue regeneration membranes in e.g. dentistry.

According to a further aspect of the present invention there is provided a method of osseous generation or regeneration comprising: making a device as described hereinabove, preferably a device comprising a customised scaffold; filling the cavity defined between the inner and outer portions of the scaffold with a filler material; seeding the scaffold with tissue cells; and implanting the scaffold in an osseous environment in a human or animal patient.

Some embodiments of the present invention will now be described, by way of example only, and with reference to the accompanying drawings, in which.

FIGS. 1a-1c give an overview of how a long bone such as a femur can be modelled when fabricating a customised scaffold. The basic anatomy of the bone, as seen in the perspective view of FIG. 1a and cross-sectional view of FIG. 1b, comprises the outer compact bone 2, the inner spongy bone 4 and the medullary cavity 6 in the centre where the bone marrow is located. This basic structure can be modelled, as shown schematically by FIG. 1c, as two generally concentric sets of walls. A central channel 8 can be dimensioned to match the medullary cavity 6. The average human bone medullary cavity is 20 mm in diameter. A cavity 10 between the two sets of walls can be filled with a porous material to match the spongy bone 4. One example of a scaffold modelled in such a way is seen in more details in FIGS. 2 and 3.

Figure 2:
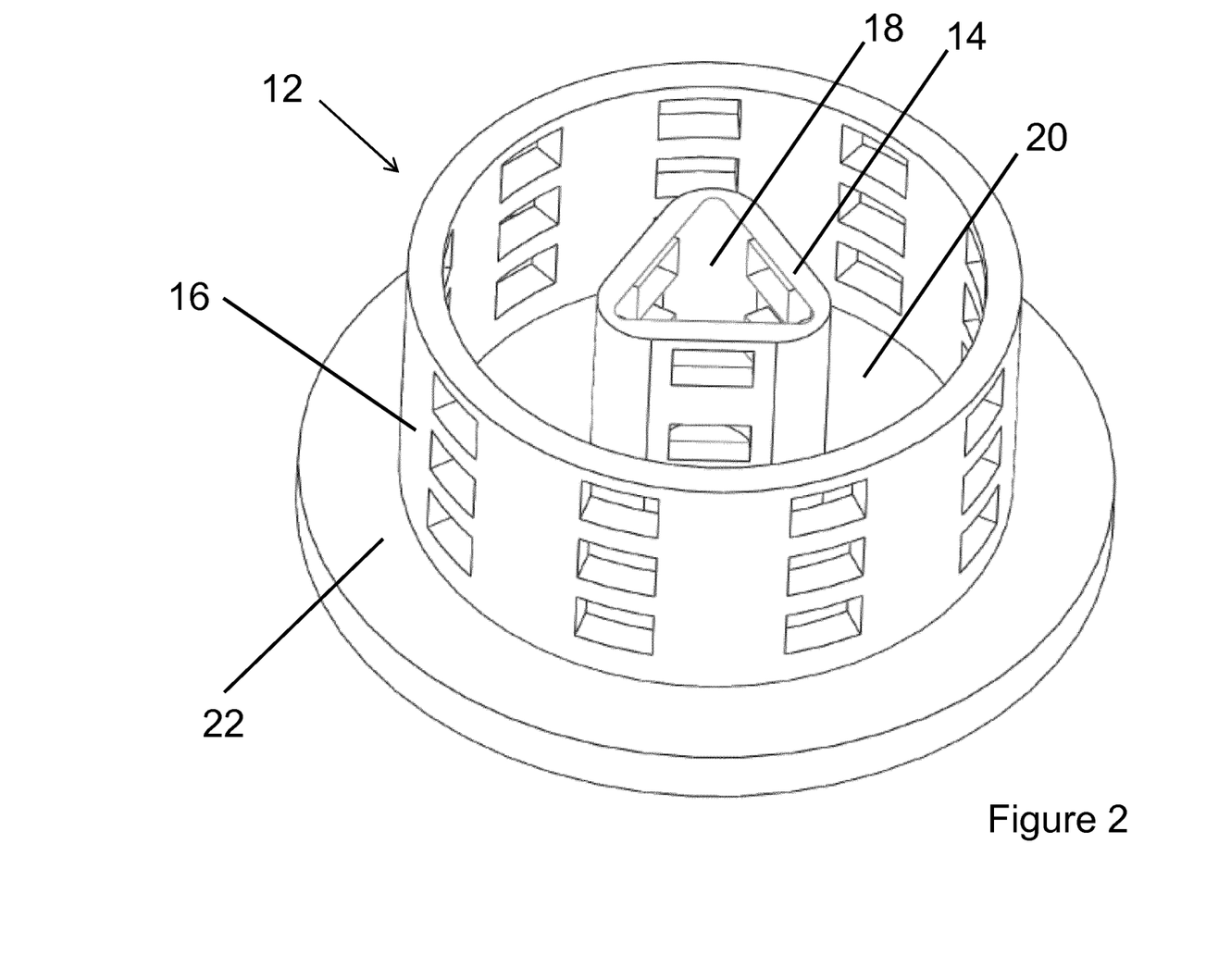
FIG. 2 is perspective view of a scaffold according to an embodiment of the present invention.

FIG. 2 shows a scaffold 12 comprising an inner portion in the form of a centric tube 14 and an outer portion in the form of a contour tube 16. In this example the centric tube 14 is shown as a triangular tube but the inner portion may be fabricated to have any suitable shape, for example cylindrical. Also, in this example the contour tube 16 is shown as a cylindrical tube but it may have any suitable cross-sectional shape. In particular, where the scaffold 12 has been customised to substantially match a target bone then its shape and/or dimensions may be tailored accordingly. Furthermore, the scaffold may include more than one contour tube 16, for example a number of concentric cylinders arranged inside one another. The walls of the centric tube 14 surround a central channel 18 extending through the scaffold 12. An annular cavity 20 is defined between the inner and outer portions 14, 16. The main function of the contour tube 16 is to support material that may be contained and/or grown in the cavity 20.

The concentric tube portions 14, 16 are connected by a base plate 22. As is seen more clearly from FIG. 3, the base plate 22 is a generally circular disc comprising a central window 24 that is shaped to match the central channel 18. In this example the window 24 comprises an opening in the material of the base plate 22. Fluid can therefore flow longitudinally through the scaffold 12, i.e. through the window 24 and along the central channel 18. The base plate 22 can be made to different diameters, for example to help incorporate the scaffold 12 into a particular device or fit an intended container such as a cell culture plate or bioreactor chamber.

Figure 3:
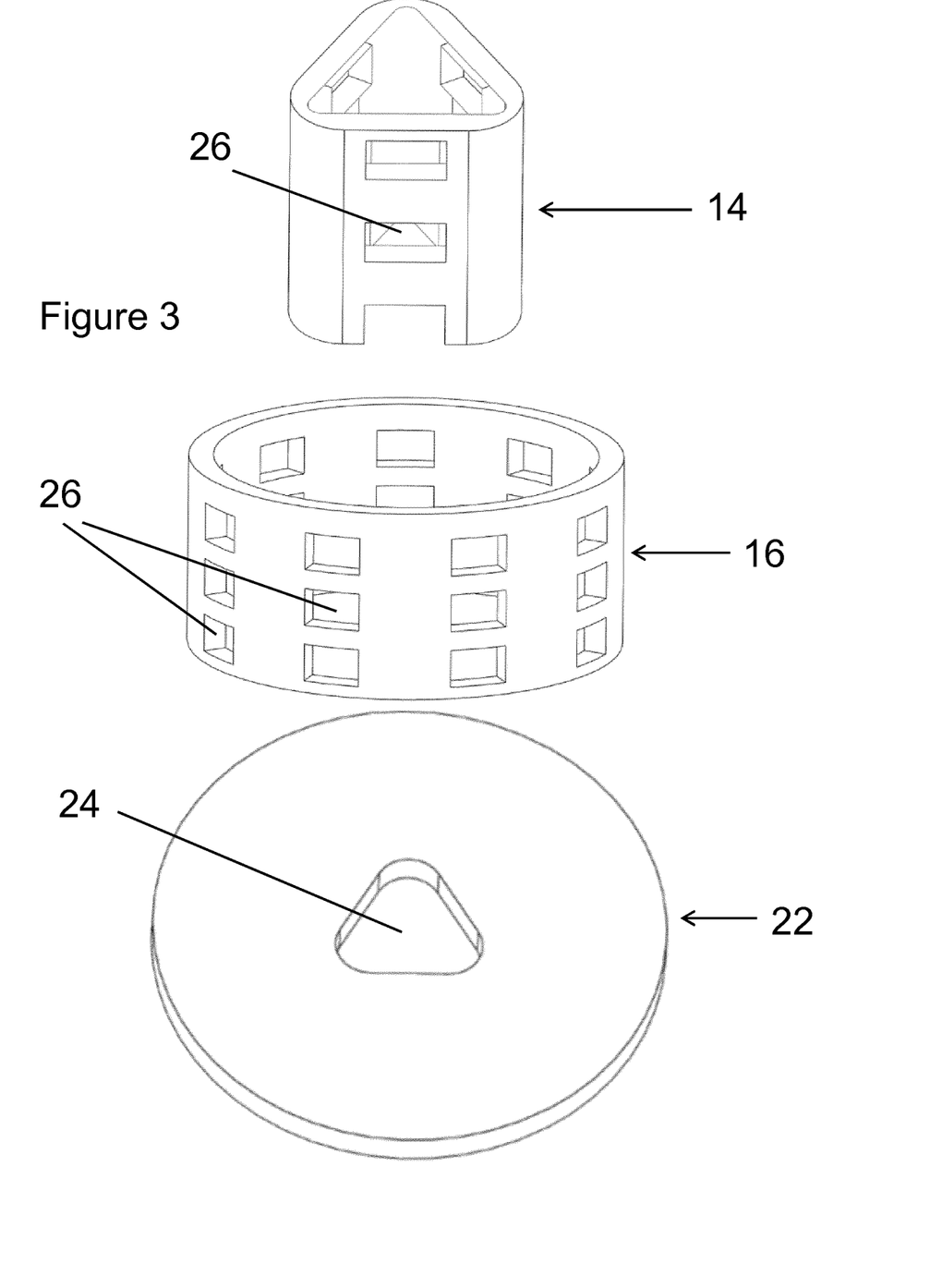
FIG. 3 is an exploded view of the components making up the scaffold of FIG. 2.
Figure 4A:
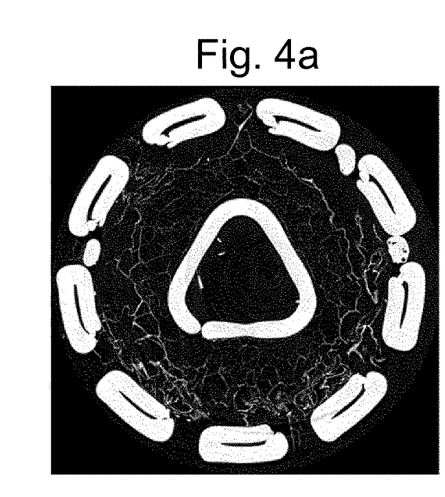
FIGS. 4a-4c are micro-CT images of the scaffold, showing the architecture of different layers at different heights in the scaffold.
Figure 4B:
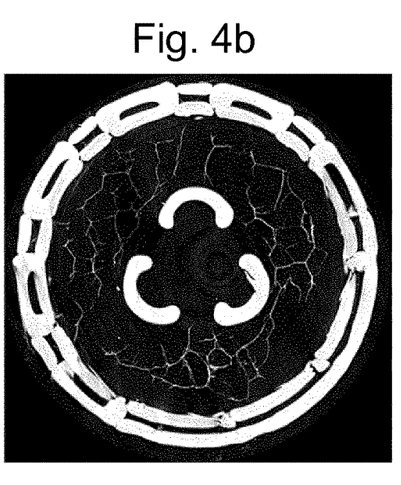
Figure 4C:
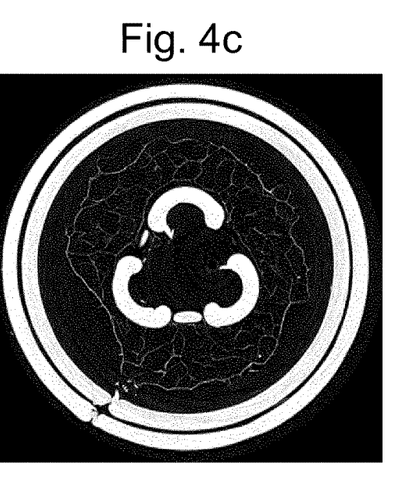

It can be seen in both FIGS. 2 and 3 that circumferential apertures 26 are provided in both the inner and outer tubes 14, 16. The apertures 26 are opened on alternate layers. For example, there are apertures 26 open in first and second layers of the inner tube 14 while first and second layers of the outer tube 16 are continuous, then there are apertures 26 open in third and fourth layers 3 and 4 of the outer tube 16 while third and fourth layers of the inner tube 14 are continuous. This may be understood more clearly with reference to FIGS. 4a-4c. This alternating arrangement of the apertures 26 ensures that there is sufficient radial diffusion available through the scaffold 12 at any given height. It can also be seen from FIGS. 4a-4c that the outer tube 16 may be fabricated with a double wall thickness as compared to the inner tube 14. This helps to provide the outer tube 16 with increased mechanical strength. The apertures 26 may be formed by an interruption in the layering process used to deposit the polymer material of the inner and outer tubes 14, 16. Accordingly each aperture 26 may have a height corresponding to an integer number of the fabrication layers, for example a height of two layers as deposited by a 3D printer.

The inner and outer tubes 14, 16 are both made from biocompatible polymer materials. The same material may be used for both tubes 14, 16, or different materials may be used so as to provide different mechanical strengths. The base plate 22 is formed from a pattern of polymeric microfilaments, for example a layering pattern of 60 degrees incrementally (0/60/120 degrees alternatively). Of course the angle and/or distance between the filaments can be controlled to give a desired degree of porosity. The base plate 22 therefore provides a mesh that can contain filler material in the cavity 20 while also connecting the inner and outer tubes 14, 16.

In such a scaffold 12 the inner channel 18 can provide for blood vessels and nutritional transfer/diffusion, allowing a culture medium to penetrate through the scaffold 12. The cavity 20 between the inner and outer tubes 14, 16 can be filled with one or more porous materials e.g. to form a sponge structure that mimics the spongy bone.

Note that the top of the scaffold 12 may be left open, as shown, or optionally be closed by a cover plate similar to the base plate 22.

EXAMPLE

A scaffold was made from a customised reproducible design recorded in a CAD model using standard CAD software such as Solidworks, AutoCAD, ProE, Magics, etc. The design was recorded in STereoLithography (STL) file format and the dimensions confirmed with reference to images of a real bone. Alternatively the design could have been recorded according to the Additive Manufacturing File Format (AMF) standard or OBJ geometry format instead of the STereoLithography (STL) file format. The STL file was then read and transferred to a 3D slicer software (such as Slic3r, Bioplotter RP, Cura, etc.) to be divided to a layer-by-layer structure. The sliced designs were then imported into RP software for fabrication by a rapid prototyping (RP) machine such as a 3D printer.

Two polyesters were used to manufacture the scaffold 12. The inner portion 14 was made from a copolymer of poly(lactide-co-caprolactone) ordered from Purac®. The outer portion 16 and the base portion 22 were made from polylactide. Polylactide was chosen for the main load-bearing parts of the scaffold 12 as it has a modulus much higher than that of the copolymer used to make the inner portion 14 defining the central channel 18. The cavity 20 between the inner and outer portions 14, 16 was filled with nanofibrous (TEMPO-oxidized nanocellulose) sponge fabricated by freeze-drying an injected hydrogel solution of gelatin/CNF. Post-modification and cleaning steps prepared the scaffold for cell seeding. For cell culture, L929 (fibroblasts) was mixed with the freeze-dried nanocellulous sponge.

Figure 5:
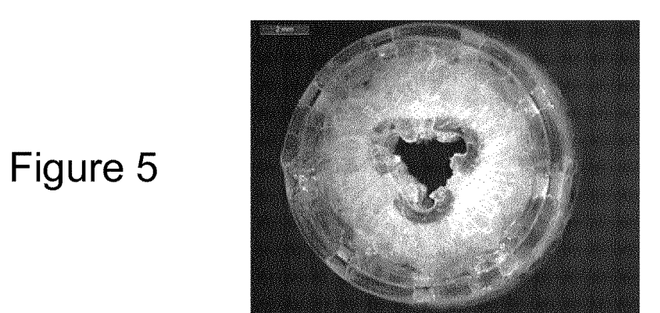
FIG. 5 is a top view image of a scaffold made and filled according to the Example given below.

Scanning electron microscope images taken 1 and 3 days after cell seeding showed positive attachment of the cells and proliferation behaviour. FIG. 5 shows the cell culture growth on the scaffold 12.

In this example the scaffold 12 was made to fit a 48-well plate in a bioreactor. The outer contour tube 16 had an outer diameter of 11.4 mm and a height of 5.0 mm. The inner triangular tube 14 had a side length of 3.5 mm and the same height of 5.0 mm. The apertures 26 in both the inner and outer tubes 14, 16 had a length of 1.5 mm and a height of 0.68 mm, corresponding to two layers of thickness 0.34 mm (as set by the RP machine). The base plate 22 included a central triangular window 24 of side length 3.5 mm to match the inner triangular tube 14. The outer diameter of the base plate 22 was 11.4 mm. The base plate 22 was made 0.68 mm thick i.e. two layers thick. It will be appreciated that the scaffold could be scaled up or down to fit any particular environment. For example, the outer diameter could be set up to 15 mm to fit a 24-well plate in a bioreactor.

The invention claimed is:

1. A device for tissue engineering comprising a scaffold, the scaffold comprising:
an inner portion comprising a central channel surrounded by a first set of one or more walls, wherein the inner portion consists of a substantially solid and non-porous material comprising a plurality of apertures in the first set of one or more walls;
an outer portion comprising a second set of one or more walls and arranged such that the second set of one or more walls substantially surrounds the first set of one or more walls with a spacing between the first and second sets of one or more walls defining an annular cavity between the inner portion and the outer portion, wherein the outer portion consists of a substantially solid and non-porous material comprising a plurality of apertures in the second set of one or more walls;
a base portion connecting the inner portion and the outer portion, wherein the base portion consists of a substantially porous material comprising a micro-filament mesh; and
a porous bone-ingrowth filler material arranged in the cavity defined between the inner portion and the outer portion and configured to support tissue cells in use;
wherein the micro-filament mesh contains the porous bone-ingrowth filler material in the cavity while also connecting the inner portion and the outer portion and providing diffusion of materials to and/or from the cavity;
wherein the base portion is a base plate that extends continuously between the inner portion and the outer portion;
wherein at least one of the outer portion or the inner portion comprises a continuous annular wall;
wherein the central channel is sized and shaped to substantially match a medullary cavity of a patient's bone;
wherein the annular cavity is sized and shaped to substantially match spongy bone that surrounds the medullary cavity of the patient's bone.

2. The device of claim 1, wherein:
the first set of one or more walls of the inner portion comprises a plurality of apertures arranged in a first set of layers spaced along a length of the first set of one or more walls by a first interval;
the second set of one or more walls of the outer portion comprises a plurality of apertures arranged in a second set of layers spaced along a length of the second set of one or more walls by a second interval;
the first set of layers is arranged to coincide with the second intervals between the second set of layers; and
the second set of layers is arranged to coincide with the first intervals between the first set of layers.

3. The device of claim 1, wherein the central channel of the inner portion comprises a triangular channel surrounded by the first set of one or more walls, and the outer portion comprises a cylindrical wall surrounding the triangular channel.

4. The device of claim 1, wherein the second set of one or more walls is thicker than the first set of one or more walls.

5. The device of claim 1, wherein the base portion comprises a window at least partially aligned with the central channel, and the window comprises an opening in the base portion.

6. The device of claim 1, wherein the porous bone-ingrowth filler material comprises one or more hydrogel materials.

7. The device of claim 6, wherein the porous bone-ingrowth filler material comprises a cellulose nanofibril (CNF) hydrogel or nanocellulose hydrogel.

8. The device of claim 1, wherein the scaffold is made using a computer-controlled fabrication technique.

9. The device of claim 1, wherein the scaffold is made using a 3D fiber deposition (3DF) method.

10. The device of claim 1, wherein the scaffold is customized to match dimensions of a particular osseous environment in a human or animal target.

11. The device of claim 1, wherein the porous filler material is seeded with tissue cells.

12. The device of claim 1, wherein the porous filler material is arranged in the cavity to form a sponge structure that mimics spongy bone surrounding the medullary cavity.

* * * * *